United States Patent [19]

Gortinskaya et al.

[11] 3,961,058
[45] June 1, 1976

[54] ANTIDEPRESSANT MEDICINAL PREPARATION

[76] Inventors: Tatyana Vladimirovna Gortinskaya, proezd Serova, 3, kv. 47; Mikhail Davidovich Mashkovsky, Leningradsky prospekt, 75a, kv. 55; Antonina Ivanovna Polezhaeva, 13 Parkovaya ulitsa, 25, korpus 1, kv. 44; Valentina Georgievna Nyrkova, Khersonskaya ulitsa, 7, korpus 1, kv. 20; Larisa Nikolaevna Bondar, ulitsa Gorkogo, 53, kv. 42; Galina Nikolaevna Litova, Novo-Khoroshevskoe shosse, 53, kv. 31, all of Moscow, U.S.S.R.; Maria Nikolaevna Schukina, deceased, late of Moscow, U.S.S.R.; Maria Nikolaevna Preobrazhenskaya, administrator, Rostovskaya naberezhnaya, 3, kv. 105, Moscow, U.S.S.R.

[22] Filed: Apr. 22, 1974

[21] Appl. No.: 463,169

[52] U.S. Cl. .......................... 424/248; 260/244 R
[51] Int. Cl.² ............................. A61K 31/535
[58] Field of Search .................... 424/248; 260/244

Primary Examiner—Stanley J. Friedman
Attorney, Agent, or Firm—Holman & Stern

[57] ABSTRACT

An antidepressant medicinal preparation comprises as an active principle, dihydrochloride-2-(2'-diethylaminoethoxy)-10-methyl-3,4-diazaphenoxiazine having the following formula:

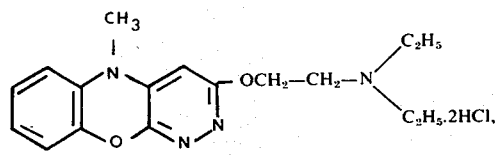

and which is combined with a pharmaceutical carrier.

6 Claims, No Drawings

ANTIDEPRESSANT MEDICINAL PREPARATION

The present invention relates to a novel antidepressant medicinal preparation.

In accordance with the invention, the preparation comprises as the active principle, dihydrochloride-2-(2'-diethylaminoethoxy)-10-methyl-3,4-diazaphenoxazine having the following structural formula:

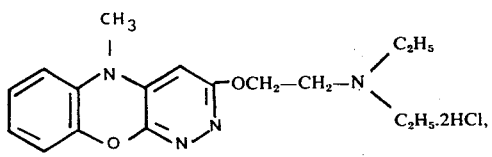

and which is combined with a pharmaceutical carrier.

Experimental animals were tested with the preparation of this invention, and it was found to produce certain effects similar to those of the tricyclic antidepressants, such as Imipramine or Amitriptyline. The novel preparation was tested on mice and found to reinforce the central effects of an Amphetamine (hyperthermia and group toxicity), to lessen the depressing effect of Reserpine, and to alleviate experimental Phenothiazine-induced catalepsy.

The proposed preparation has no cholinolytic effect, nor does it inhibit the monoaminoxidase activity. The preparation is characterized by a low toxicity level. When administered to white mice intravenously, its $DL_{50}$ is 34 mg/kg body weight and per os, 580 mg/kg.

When compared with the prior art antidepressants, such as Imipramine or Amitriptyline, the proposed preparation is experimentally found to have a less marked anti-Reserpine effect and to produce no effect on the vegetative nervous system. Clinically, the preparation of this invention is effective for treating various types of depression, as well as for a stimulating and energizing drug offering the additional advantage of having low toxicity.

In clinical application, the proposed preparation is a mild antidepressant which, along with the thymoanaleptic properties, has a positive stimulating and energizing effect, thus activating the patients, boosting their psychic activity and reducing their apathy.

The preparation of this invention was studied on 469 patients classified, in terms of pathology, as follows: schizophrenia, 216; circular depression, 20; reactive depression, 43; depression with organic brain lesions, 125; depressive-paranoidal reactions in involution, 12; depression of vascular genesis, 13; psychogenic depression, 17; and manic-depressive psychosis, 42. In addition, the preparation has been used in cases of neutrasthenia, climacteric insanity, hysteria, etc.

Analysis of the preparation's effectiveness produces the following analysis: considerable or noticeable improvement, 283 patients; temporary effect or insignificant improvement, 119 patients; no effect, 67 patients. The preparation proved to be the most effective in cases of asthenic and astheno-depressive syndromes of neurasthenic genesis, as well as in shallow depressions accomapanying recurrent schizophrenia or manic-depressive psychosis. Asthenic and listless patients were stimulated by the preparation. The preparation was the least effective or totally ineffective in deep, and prolonged depressions.

When patients with a depressive-paranoidal syndrome were given the preparation, then sometimes caused exacerbation of paranoidal and hallucinatory disturbances.

The proposed preparation can be most advantageously employed in cases of medium and mild depressions accompanied by adynamy and asthenia, as well as listless-apathetic, and apatho-aboulic states.

The preparation of the invention comprises an active principle combined with a carrier such as a tablet filler of starch or confectioner's sugar. The amount of the active principle in one tablet is around 0.025 mg.

The preparation is prescribed per os in the form of powders or tablets, with the initial doses ranging from 25 to 50 mg.

The optimal dose is from 100 to 150 mg, with the maximal daily dose being from 300 to 400 mg. The course of treatment lasts from 45 to 60 days, followed by a prolonged (up to one year) course of small doses (from 50 to 100 mg).

The proposed preparation is usually well tolerated by patients. In some cases it may have side effects, such as headache, dryness of mucous membranes and general weakness.

In patients with paranoidal and hallucinatory disorders, the preparation is liable to intensify delirium and hallucinations.

Due to the stimulating effect of the preparation, it should not be taken in the evening. The proposed preparation is contraindicated in cases of acute inflammatory disorders of the liver, as well as in disturbances of the excretory function of the kidneys.

The preparation should not be prescribed together with monoaminoxidase inhibitors.

The acitive principle of the proposed preparation, dihydrochloride 2-(2'-diethylaminoethoxy)-10-methyl-3,4-diazaphenoxazine, is produced as follows: a solution of 2-diethylaminoethylate of sodium and 2-chloro-10-methyl-3,4-diazaphenoxazine is boiled for 5 hours, whereupon the resulting 2-diethylaminoethynol is distilled under vacuum, and the residue is washed with water in order to yield the desired product having a melting point of 111° to 112°C. In order to obtain dihydrochloride 2-(2'-diethylaminoethoxy)-10-methyl-3,4-diazaphenoxazine, the base thusly obtained is dissolved in ethylacetate and a certain amount of an alcohol solution of hydrogen chloride is added.

Estimated in wt.% are: N, 13.84; Cl, 17.50; Actual in wt.% are: N, 13.45; Cl, 17.86; $C_{17}H_{22}N_4O_2 \cdot 2HCl$.

The preparation of the invention may be manufactured by any prior art technique.

The preparation is to be kept in a dry and cool place.

What is claimed is:

1. An antidepressant medicinal composition, consisting essentially of an effective amount of the compound dihydrochloride 2-(2'-diethylaminoethoxy)-10-methyl-3,4-diazaphenoxazine of the following formula:

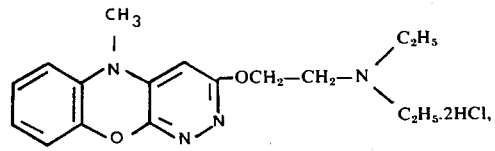

combined with a pharmaceutical carrier.

2. A medicinal composition as set forth in claim 1, wherein the carrier is in tablet form, and is selected from the group consisting of confectioner's sugar and starch.

3. A medicinal composition as set forth in claim 1, wherein the compound is contained in an amount of 0.025 mg per os.

4. The medicinal composition, as claimed in claim 2, wherein the compound is contained in an amount of 0.025 mg per tablet.

5. The medicinal composition, as claimed in claim 1, wherein the compound is contained in an amount of from 0.025 to 400.00 mg.

6. The medicinal composition as claimed in claim 2, wherein the compound is contained in an amount of from 0.025 to 400.00 mg.

* * * * *